United States Patent [19]

Rollwitz

[11] Patent Number: 4,608,991
[45] Date of Patent: Sep. 2, 1986

[54] METHOD FOR IN-VIVO NMR MEASUREMENTS IN THE HUMAN BREAST TO SCREEN FOR SMALL BREAST CANCER IN AN OTHERWISE HEALTHY BREAST

[75] Inventor: William L. Rollwitz, San Antonio, Tex.

[73] Assignee: Southwest Research Institute, San Antonio, Tex.

[21] Appl. No.: 654,956

[22] Filed: Sep. 26, 1984

[51] Int. Cl.⁴ .................................................. A61B 5/05
[52] U.S. Cl. .................................................. 128/653
[58] Field of Search ............... 128/653, 660, 702, 704; 324/307, 309, 318, 319, 321, 312

[56] References Cited

U.S. PATENT DOCUMENTS

| 2,878,444 | 3/1959 | Feher | 324/321 |
| 3,556,081 | 1/1971 | Jones | 128/660 |
| 3,774,102 | 11/1973 | Utsumi et al. | 324/318 |
| 3,789,832 | 2/1974 | Damadian | 128/653 |
| 4,240,439 | 12/1980 | Abe et al. | 128/653 |
| 4,354,499 | 10/1982 | Damadian | 128/653 |
| 4,379,262 | 4/1983 | Young | 324/309 |
| 4,412,179 | 10/1983 | Brown | 324/312 |
| 4,422,042 | 12/1983 | Sugimoto | 324/319 |

FOREIGN PATENT DOCUMENTS

| 3204852 | 8/1982 | Fed. Rep. of Germany | 128/653 |
| 3140225 | 4/1983 | Fed. Rep. of Germany | 128/653 |
| 0203634 | 10/1983 | Fed. Rep. of Germany | 324/307 |
| 3323657 | 1/1984 | Fed. Rep. of Germany | 128/653 |
| 2091884 | 8/1982 | United Kingdom | 324/307 |
| 2101327 | 1/1983 | United Kingdom | 324/307 |

Primary Examiner—Kyle L. Howell
Assistant Examiner—Ruth S. Smith
Attorney, Agent, or Firm—Gunn, Lee & Jackson

[57] ABSTRACT

A method and apparatus for testing for cancer cells in the human breast is set forth. In the preferred and illustrated embodiment, a pendulant breast exposed to a magnetic field is tested by nuclear magnetic resonant (NMR). The magnetic field is varied to provide the requisite field intensity in selected segmented sections of the pendulant breast within the field. The field intensity is varied to thereby observe all of the breast extending toward the thorax cavity, obtaining test data from section after section aggregating test data from the entire breast within the pole pieces of the magnet and sufficiently therebeyond to obtain full interrogation. The NMR response focuses on hydrogen nuclei in the water in the breast region, determines the voltage proportional to the density of hydrogen nuclei and the binding of the water described by the relaxation times $T_1$ and $T_2$ for each binding level for water. The data so obtained in sequence is examined. Difference values from sequentially obtained signals are evaluated, yielding a plot of different signals as a function of breast length, thereby yielding abnormalities. Such abnormalities are shown in the difference signal from NMR interrogation as a result the concentration and relaxation time ($T_1$ and $T_2$) changes in tumo 15 Claims, 6 Drawing Figures

METHOD FOR IN-VIVO NMR MEASUREMENTS IN THE HUMAN BREAST TO SCREEN FOR SMALL BREAST CANCER IN AN OTHERWISE HEALTHY BREAST

BACKGROUND OF THE DISCLOSURE

Nuclear magnetic resonant (NMR) is a test procedure which does not involve invasion of the human body. It can be implemented risk free without side effects or cumulative exposure problems. The signals obtained from it can be recorded and subsequently analyzed.

With these advantages in mind, the present apparatus and method set forth a safe breast cancer detection system. This apparatus is particularly capable of detecting tumorous masses in the human breast, a both malignant and benign. A particular advantage of the present apparatus is the fact that it can make relatively quick measurements without bodily invasion, thereby yielding tumor information. It has been discovered that a significant portion of the tissue in the region of the breast (both normal tissue and tumorous tissus) is made up of water. There are differing binding levels for the hydrogen in the water. The tissue of interest provides one response if the tissue is normal. A different response is provided by cancerous tissue. The difference shows up in comparison of signals obtained from adjacent slices or segments interrogated by NMR techniques. In other words, the data from a first slice is subtracted from data obtained from the adjacent second slice to yield a first difference signal. Second and third difference signals are obtained in like fashion. The signals are graphed as a function of breast length to locate the position within the breast of each data point, and to further isolate anomalies in data indicative of tumors.

This apparatus and the method related thereto utilizes NMR interrogation for the express purpose of obtaining data derived from the hydrogen (water) concentration and the spin-lattice or the spin-spin relaxation times of hydrogen, often identified by the constants $T_1$ and $T_2$. Through this analysis, the concentration of loosely bound water in the body tissue can be determined. Equally, the concentration of more tightly bound water in the body tissue can be determined.

As a means of placing the equipment in near proximity so that data can be obtained, the present invention contemplates the use of a changing magnetic field. This can be obtained by forming a fixed magnetic field of proper field intensity and moving the magnet toward the patient undergoing testing. One alternative to this is to utilize a fixed magnet and vary the magnetizing current, thereby changing the field intensity and creating a segment of the field of proper field strength. Alternate arrangements utilizing combinations of changing field current or magnet location will enhance the investigation procedure set forth herein.

The changing field enables an isolated portion of the body tissue to be examined. It takes advantage of the relationship obtained from the frequency of the interrogation pulse and magnetic intensity. For a given frequency, there is a single magnetic intensity. If the field is shaped with a gradient, only a portion of the field will define the proper magnetic intensity. This intensity is identified by the symbol $H_o$. This field intensity is found in a region within the magnetic field, and does not normally encompass the entire magnetic field region. Rather, the field has other values of intensity (radiofrequency magnetic field), identified by the symbol $H_1$. This magnetic field intensity is neither too weak or too strong but sufficient to cause the transient NMR effect desired. This magnetic field intensity must be of sufficient magnitude to accomplish the necessary NMR response. The magnetic field gradient is used to advantage to thereby limit the portion of body tissue exposed to NMR interrogation. This portion can be described as a thin slice of body tissue. The thickness of the slice can be controlled dependent on the magnetic field gradient. Ideally, the slice is relatively thin, typically even as thin as one millimeter. By changing the relative position of the proper magnetic field intensity $H_o$, sequential slices of the breast region can then be observed, tested and anomalies identified. Assuming a maximum breast length of perhaps 15 centimeters, this provides about 150 segments of one millimeter thickness. Assuming that there is a measure of overlap between each test interrogation, perhaps as many as 300 data points might be obtained. A short interval is required to obtain each data point because the polarization time for the hydrogen nuclei making up the body tissue is relatively short, and the perturbations arising from each prior pulsed NMR interrogation is relatively short lived.

With the foregoing in view, the present apparatus is summarized as a structure including an examination table having a hole or holes therein to enable a patient undergoing tests to recline on the table, placing one breast or both breasts through openings in the table. This extends the breast and assures that the breast is within the operating range of the NMR test equipment. Multiple test points are obtained. The magnetic field intensity is varied so that the field intensity segments the breast into a number of relatively thin test volumes, each having a relatively thin dimension and each comprising a relatively thin slice. The test apparatus includes a magnetic field controller. This controls the current applied to the electromagnet to thereby define the field. A transmitter forms a pulse at a selected frequency which is applied to a coil. The coil is positioned so that it surrounds the breast, enabling the breast to be inserted into the coil volume for interrogation.

The equipment also includes a NMR receiver connected to the coil. The receiver is output to a circuit measuring the difference between consecutive received signals. This difference is supplied to a recorder which records the different signals as a function of breast length. Breast length is defined as the dimension of the magnetic field area wherein the breast is placed. Inasmuch as multiple data points are obtained, the output of the apparatus is a signal which is a function of length. Anomalies in the difference signal are indicative of a tumor or other mass causing distortion in the data arising from differences in tightly bound and loosely bound water within the body tissue.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
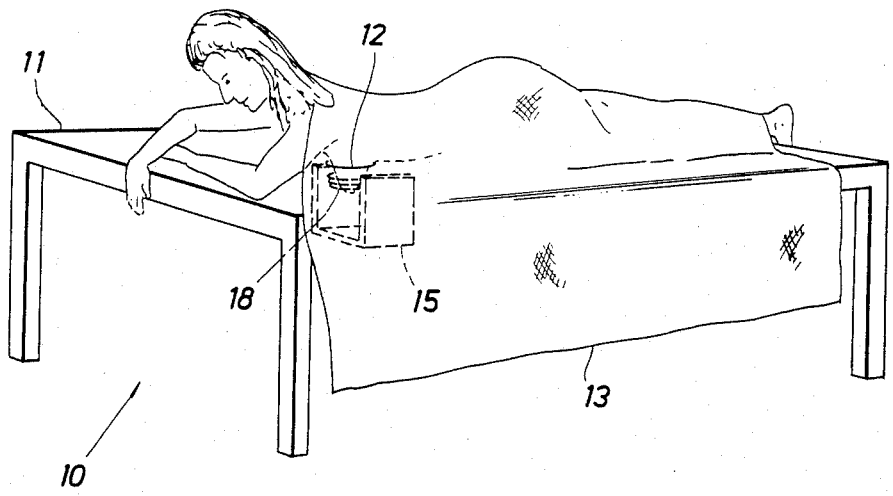
FIG. 1 shows a patient undergoing examination with the NMR breast test apparatus of the present disclosure.

Attention is first directed to FIG. 1 of the drawings. There, a table which comprises a portion of the test apparatus is shown. The test apparatus 10 includes an examination table 11. A circular hole 12 of appropriate diameter is formed in the table, and the table is typically covered with resilient padding and cloth for the comfort of the patient. The patient reclines on the table in the manner shown in FIG. 1 positioning one breast in the opening 12 so that it will hang in pendulant fashion into the opening and extend through the opening for examination. The length of the breast is herein defined as a measure along the center line of the opening 12. This refers to the length or extent of the breast as it hangs by gravity into the opening, thereby being exposed for examination by the NMR test technique. This test technique utilizes multiple interrogations of the breast extending through the opening. In addition, the sensitive volume as will be defined hereinafter extends upwardly toward the thorax cavity, thereby assuring that a significant portion of the breast is examined, also including within this examination that area of the breast which is located immediately adjacent to the rib cage and sternum.

The test equipment further includes a detection coil and magnet as will be described. One embodiment of the procedure contemplates testing of first one breast and then the other through the use of the use equipment. Another embodiment uses one magnet with two detection coils, one for each breast. For the first embodiment, the opening 12 is located more or less toward the center of the table so that the patient undergoing testing can conveniently lay adjacent to the table opening for testing of both breasts. Such testing can be conveniently undertaken with only partial disrobing and convenient covering with a spread or sheet 13 for benefit of the patient without interferring with the performance of the test. If desired, for personal comfort the breast could also be covered by a thin gauze bra without seriously influencing the desired results.

Figure 2:
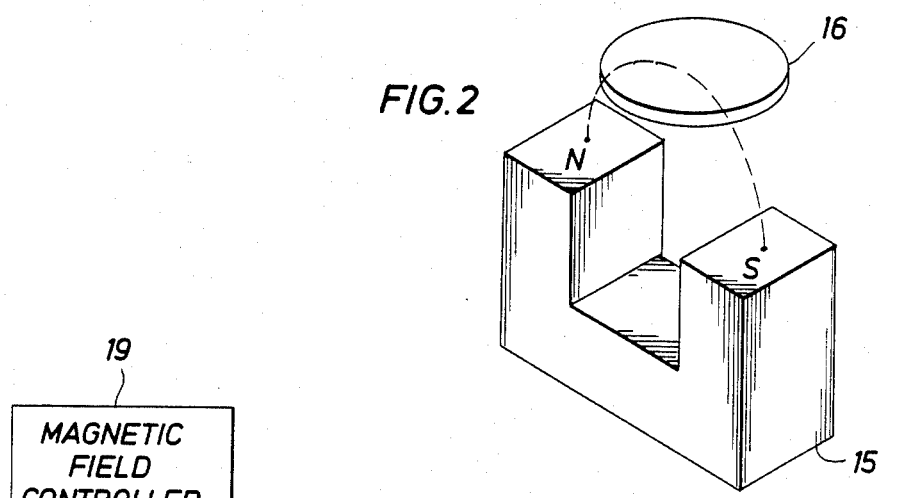
FIG. 2 is a perspective view of a magnet forming a magnetic field having a field intensity defining a sensitive volume undergoing tests.

Before describing the remainder of the equipment in detail, it would be helpful to understand the interplay between the interrogation pulse frequency and magnetic field intensity. For a given frequency, there is one thin range of magnetic field intensities appropriate to obtain resonance of the hydrogen nuclei. In other words, frequency is proportional to field intensity. The magnet is therefore preferably operated to define a sensitive volume within a region defined by intensity $H_o$ and the range of magnetic field $\Delta H_o$. In FIG. 2 of the drawings, the numeral 15 identifies a magnet having north and south poles which forms magnetic flux lines between the poles. The flux lines defining the proper magnetic field intensity are identified at $H_o \pm \Delta H_o$. This intensity passes through the breast area in the gap or area above or between the magnet poles.

This specific intensity defines the sensitive volume 16. The sensitive volume is thus limited more or less to a circle of width $\Delta H_o$, this being the volume of the breast where the field intensity is the proper measure or is $H_o \pm \Delta H_o$. The field intensity at $H_o \pm \Delta H_o$ thus defines the sensitive volume. The thickness can be controlled by altering the magnetic field gradient to control $\Delta H_o$. The diameter of the sensitive volume 16 varies from patient to patient and is also susceptible to variation with of the posture of the patient. The volume 16 is assumed to be circular but it may be less than perfectly round for various individuals. The sensitive volume thus defines the full diameter of the breast at the proper magnetic field intensity $H_o$; it is optimum in the use of this apparatus to define the sensitive volume as a finite thickness which is relatively fixed; as a suggestion but not as an absolute requirement, a thickness of about one millimeter will suffice. This dimension can be varied by changing $\Delta H_o$. In like fashion, the diameter of the sensitive volume 16 shown in FIG. 2 is dependent on the size, shape and configuration of the patient, and will range from zero up to some maximum value.

As observed in FIG. 2, the sensitive volume 16 is moved so that all portions of the breast are scanned. Movement can be obtained either by moving the magnet up and down, or alternatively changing the magnetizing current to change the location of the requisite field intensity symbolized at $H_o$. Other magnetic field intensities identified as $H_1$ have no interaction with the RF magnetic field frequency as will be described.

Figure 3:
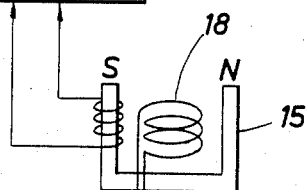
FIG. 3 is a schematic block diagram of the NMR test circuitry.
Figure 3:
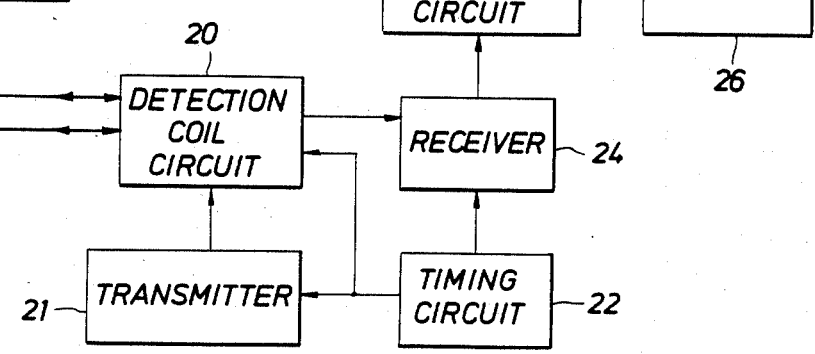

Attention is next directed to FIG. 3 of the drawings. There, a schematic block diagram is set forth the purpose of detailing the construction of the device. In FIG. 3, the numeral 15 identifies the magnet. It should be kept in mind that FIG. 3 is a symbolic representation of the magnet. The magnet field forms both internal and external volumes. The internal volume is just below the opening 12 in the examination table 11. The breast extends into the area between the pole pieces of the magnet. The breast further extends centrally along the axis of the detector coil 18. The field intensity is determined by magnetic field controller 19. This is connected to the coils defining the magnet 15 and furnishes a current to vary the field intensity. The concentric detector coil 18 is connected with a detection coil circuit 20. It is connected to a transmitter circuit 21. It forms interrogation pulses in timed sequence under control of a timing circuit 22. The circuit 22 causes the transmitter 21 to form interrogation pulses which are supplied through the detector coil circuit 20 and are applied to the detection coil 18. Such pulses are input for the coil to transmit the necessary field. The detection coil circuit 20 switches the coil 18 after transmission for receiving data; the data is output from the circuit 20 to a receiver 24, and the signal amplitude is output by the receiver 24. The received signal output is supplied as a function of time to a difference signal circuit 25. This circuit stores a first received signal, obtains a second and sequential received signal, measures the difference between the two and forms a difference signal output to a recorder 26. The recorder 26 records the data. The recorder 26 stores in suitable format a plot of difference signals as a function of breast length, thereby focusing on signal anomalies indicative of a cell or growth within the breast.

Figure 4:
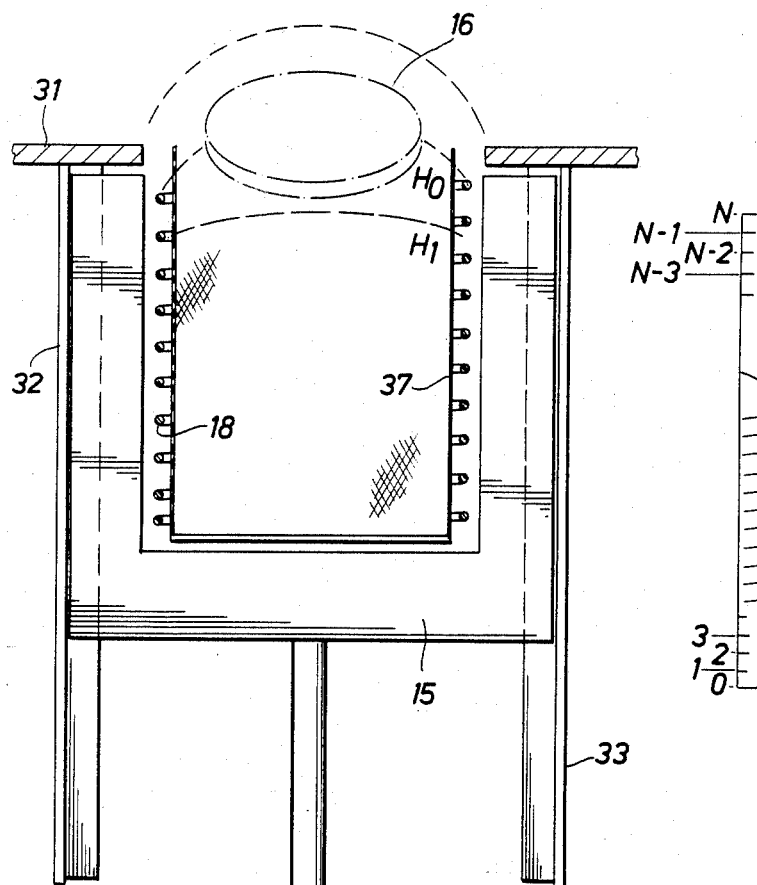
FIG. 4 shows one form of apparatus moving a magnetic field gradient so that the sensitive volume is moved over a period of time to examine the entire breast.

Attention is directed to FIG. 4 of the drawings. There, the numeral 30 identifies the structure shown in FIG. 4 to be a scanning apparatus to assure that different areas of the breast are scanned for NMR response. To this end, the apparatus shown in FIG. 4 is especially made to move the magnet toward the patient undergoing observation to bring the magnet steadily along the length of the breast to vary the location of the sensitive volume, assuring testing of the entire breast. The structure of FIG. 4 shows the top of the table at 31. Beneath the table, facing angle frame members 32 and 33 function as guides for the magnet. They are spaced so that they guide the magnet 15 in upward and downward movement. Preferably, the magnet 15 is captured between upstanding vertical members so that it is guided without wobble or canting. It travels to the uppermost position which is immediately below the table top 31, and it retracts downwardly by a distance sufficient to scan the full length of the breast. As a suggestion, to encompass a wide range of breast lengths, a travel or stroke of 150 millimeters will typically suffice. Moreover, the magnet 15 is typically guided by or among four angle members arranged at the four corners at the magnet. In this construction, it is presumed that the magnet is rectangular in cross-section having four corners, and is located within the guides which enable the magnet to travel vertically. The magnet is preferably moved by any suitable motive means, and one convenient apparatus is a double acting piston and cylinder construction as identified at 35. The magnet is supported on a piston rod 36 which extends to the magnet and connects with the magnet. Preferably, the piston rod is joined to the center of magnet so that an even force is applied to the magnet thereby preventing wobbling.

It will be further noted that FIG. 4 includes the detection coil 18 on the interior of the magnet, that is between the pole pieces. In the preferred construction, a liner of thin rubber or plastic can be positioned on the interior of the detection coil to enclose and house the detection coil. Such a liner will not impede the operation of the device, and may provide greater comfort to the patient, and also reduce the risk of pinching. The risk of pinching can also be reduced or eliminated by constructing the coil so that it is somewhat larger than the opening 12 formed in the examination table. Whatever the case, an internal liner can be conveniently positioned inside the coil.

FIG. 4 shows also a Faraday type shield 37. This shield 37 is inserted between the RF coil 18 and the pendulous breast to shield the breast from unwanted and unneeded electric fields from the coil 18. The electric fields are not needed for the magnetic resonance phenomenon. The shield 37 therefore should be such that it passes the radio frequency magnetic fields needed for the nuclear magnetic resonance but does not pass the electric fields.

FIG. 4 shows several lines of flux, all for the purpose of defining the desired magnetic field intensity $H_o$. Again, the sensitive volume 16 is shown in FIG. 4. The sensitive volume 16 is able to traverse the area below and also above the opening in the examination table and moves along the length of the breast. As it traverses, the sensitive volume 16 sweeps out a space (as integrated over a period of time from the starting point to the ending point of travel) thereby assuring that the entire volume of the breast is examined. The rate of travel of the magnet 15 should be considered. It is moved so that the sensitive volume 16 obtains data from adjacent volumetric portions. They can overlap to a degree. The ideal arrangement is that the volume 16 be relatively thin, and that adjacent data points obtained from adjacent volumes overlap slightly to assure that every portion is tested. Thus, the device will eventually acquire up to N data points, thereby defining a complete set of test data.

From the foregoing, it will be therefore be seen that the sensitive volume 16 sweeps out a volume which encompasses the region of the breast. In fact, when the patient is in a reclining position, and noting that the sensitive volume 16 is above the top end of the pole pieces, testing can occur fully to the rib cage of the patient.

Figure 5:
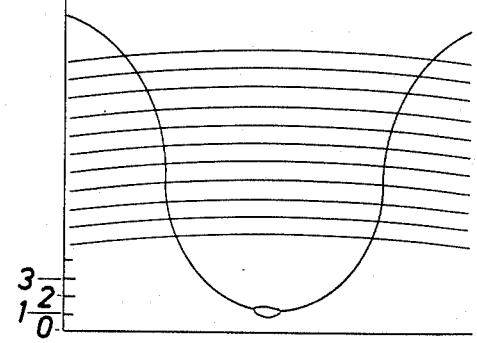
FIG. 5 is a side view of a pendulant breast showing segments of body tissue examined on different sequential tests interrogations.
Figure 6:
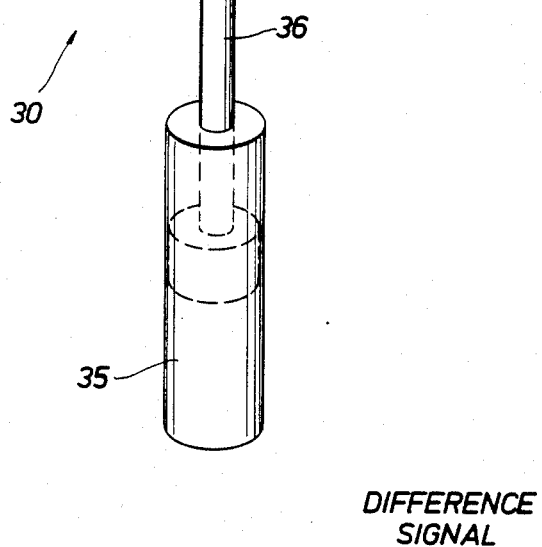
FIG. 6 is a graph of the difference signal as a function of breast length.
Figure 6:
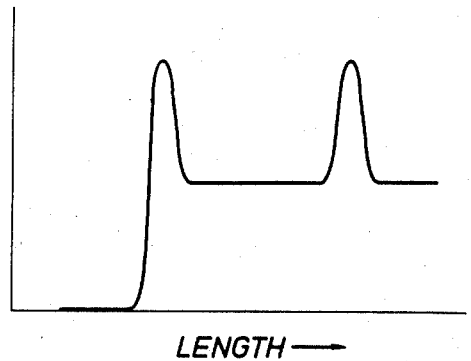

Considering now FIGS. 5 and 6 jointly, the maximum possible range of travel for the equipment is divided into N test areas or segments. This represents the location of the sensitive volume 16 along a center line axis within the detection coil. This moving volume must sweep through the entirety of a breast, the representative breast in pendulent position being shown in FIG. 5. The length of travel is the ordinate of FIG. 5 and has been divided into N segments. All the segments are slightly curved segments because the volume 16 is slightly arcuate. The curvature does not detract from the integration described. The first segment is defined at the maximum point of breast penetration into the test area. This is where N equals zero. The test sequence contemplates N equal to a specific integer to obtain a total of N data points as shown in FIG. 5. In FIG. 6, there is a plot of difference signal versus breast length. If the breast does not extend to the full length where N equals zero, no data is obtained. There is some disturbance to the shape of the curve as shown in FIG. 6 when the breast is first encountered and data is then displayed. The difference signal is exaggerated as a result of the change from no data to some output data. The difference signal is thus plotted as a function of length. The difference signal should normally show a nominal flat value except in the occurance of signal anomalies indicative of a growth. Assume that the difference signal is an arbitrary ten units from data point to data point arising from observation of a healthy breast. A disturbance in the difference signal will be indicative of a growth or tumor. This is observed because such a tumor or growth materially alters the state of water in the area of the breast. In fact, the water concentration is changed markedly so that even relatively small growths can be detected. The threshold value depends on the sensitivity of the system and will vary depending on the dimensions of the coil, the sensitivity of the receiver, the thickness of the sensitive volume, and other scale factors. The difference signal is thus recorded as a function of length so that it can be evaluated to determine whether or not further examination is required.

The type of NMR signal interrogation can be selected. One type of NMR interrogation is to observe the free induction decay (FID) signal following a single 90° pulse. The FID signal is found in the output of each data point; adjacent data points are again subtracted from one another to provide the difference signal as described hereinabove. An alternate form of interrogation is to observe the echo following a dual pulse sequence from the transmitter. This enables the characteristic relaxation time $T_2$ to be obtained. The echo amplitude thus follows a dual pulse sequence wherein the pulse pattern is 90°-τ-180°. This pattern yields relaxation time $T_2$. An alternate approach is to observe the FID amplitude following two pulses at 90° spacing while altering the spacing to enable recordation of the amplitude and thereby yielding characteristic time $T_1$.

Other interrogation techniques can be used. The pulse pattern typically contemplates one or two transmitter pulses at each data point. That is, for each of the levels of the sensitive volume 16 (ranging from level zero to level N) the data is recorded as a function of the difference between adjacent test signals. That is, up to N test points are made. The difference signal is obtained between adjacent signal outputs. The difference signal is more readily examined and easily interpreted. There is some degree of variation as a result of the factor. The factor refers to the fact that the breast is, speaking somewhat loosely, conic in shape and hence, adjacent interrogated sections of the breast are different in size or "fill" within the sensitive volume. However, if the number of data points (referring to the maximum value of N) is increased, the adjacent sections become thinner and hence more nearly uniform. That is, the rate of change between adjacent volumes is markedly reduced. This enables the "fill" factor change to be reduced significantly.

Many variations can be made in the present apparatus and method of testing. As an example, one variation is to move the sensitive volume by changing the current applied to the magnet 15. An alternate approach is to move the magnet and hence move the sensitive volume; certain portions of the breast will be exposed to magnetic field intensity which is not the required $H_o$ but this poses no problem and does not create any discomfort to the patient. The magnetic field is unobtrusive to the patient.

As a suggested rate of obtaining data, one data point can be obtained at a rate of one per second with 300 data points required to span the full maximum length of fifteen centimeters, assuming that there is approximately 50% overlap. In other words, 300 data points will more than amply cover a region of 150 millimeters length in segments which are about one millimeter thick.

Going now to the pulse repetition rate, if one data point is taken every second, this permits sufficient time for the hydrogen nuclei to be realigned after the last disturbance. The interrogation pulse typically has a pulse width between 10 and 50 microseconds. The frequency of the interrogation pulse is typically less than about 8 megahertz but there is no limitation to it being higher.

While the foregoing is directed to the preferred embodiment, the scope thereof is determined by the claims which follow.

What is claimed is:

1. A method of conducting a noninvasive female breast cancer test comprising the steps of:
   (a) forming a an inhomogeneous magnetic field between the poles of a magnet wherein the magnetic field defines a specific volume between the poles wherein the specific volume has a specified magnetic field intensity $H_o$ for NMR testing and the specific volume extends outwardly to an edge defined by the outer edge of the female breast;
   (b) moving incrementally the specific volume from a beginning point toward an ending point to scan a breast between the pole pieces of the magnet and thereby move the specific volume through the breast the movement being with N examinations located along the breast at different locations wherein each specific volume has the defined thickness and outward extent;
   (c) periodically interrogating by a transmitted pulse from a coil into the breast portion located in the specific volume for NMR response wherein the NMR response is dependent on hydrogen in the water, and the water has two states, one state in cancer cells and the other state in healthy tissue, and the cancer cells provide a different NMR response compared with water in the healthy tissue, the step of interrogating including first and second NMR interrogations of specific breast volumes forming NMR responses;
   (d) wherein the magnetic field intensity in the specific volume and the pulse from the coil cause an NMR response from water in the body tissue making up the breast portion; and
   (e) determining cancer cell anomalies arising from cancer cells in the breast as indicated by comparison of the NMR water responses to form difference signals.

2. The method of claim 1 including the step of sequentially moving the specified volume by moving the magnet relative to the breast.

3. The method of claim 1 including the step of moving the specific volume by changing the magnetizing current to the magnet to vary magnetization thereof.

4. The method of claim 1 including the step of locating the magnet beneath an examining table to enable a female to recline therein to suspend a pendulant breast for testing in the magnetic field.

5. The method of claim 1 including the step of serially moving the specific volume along a path to examine the entire breast with N examinations and the N examinations enable formation of N-1 difference signals; plotting the N-1 difference signals to locate an anomaly.

6. A method of conducting a non-invasive female breast cancer test comprising the steps of:
   (a) forming an inhomogeneous magnetic field between the poles of a magnet wherein the magnetic field defines a specific volume between the poles wherein the specific volume has a specified magnetic field intensity Ho for NMR testing;
   (b) moving incrementally from a beginning point toward an ending point the specific volume to scan a female breast by NMR testing of N specific volumes to thereby test substantially the entire female breast volume in incremental volumes;
   (c) periodically interrogating by a transmitted pulse from a coil into the breast portion located in the specific volume for NMR response;
   (d) wherein the magnetic field intensity in the specific volume and the pulse from the coil cause an NMR response from the breast portion; and
   (e) determining anomalies arising from abnormal growths as indicated by differences in NMR responses from at least two different interrogations for the N specific volumes of the female breast and proceeding incrementally in testing the female breast.

7. The method of claim 6 wherein consecutive NMR responses are subtracted to obtain a difference signal for different breast portions up to N breast portions.

8. The method of claim 6 wherein the testing is for hydrogen NMR response, and wherein the hydrogen has differing binding phases in cancerous tissue compared to normal tissue, and said method obtains NMR responses for adjacent breast portions having specific volumes of equal thickness which responses are subtracted from one another to yield a difference signal having a cancer tissue binding phase compound.

9. The method of claim 6 wherein healthy tissue water binding phase has a similar signal component in the response of two adjacent breast portion interrogations, and said similar signal components are approximately equal such that the step of determining anomalies includes subtracting and wherein said signals are subtracted, and approximately null to zero.

10. The method of claim 6 wherein adjacent breast portion responses are subtracted to obtain a difference signal having a $T_1$ component.

11. The method of claim 6 wherein the NMR response is obtained from hydrogen in water and the water in the breast tissue is relatively tightly or relatively loosely bound, and wherein the relaxation time for water in cancerous tissue is longer, the method including the step of observing anomalies indicative of cancer by comparing signals from consecutive and adjacent volumes of the female breast.

12. The method of claim 6 including the step of obtaining NMR measurements from adjacent breast portions wherein the adjacent portions have a relative volume within 5% of one another, all as obtained by hanging with the aid of gravity the female breast in the magnetic field, thereby obtaining a pendulous breast, and difference signals re obtained therefrom indicative of variations in relaxation time of hydrogen in the water in the cancerous tissue in contrast with healthy tissue.

13. The method of claim 6 wherein the interrogation obtains a FID response from the body tissue, the FID response following a dual pulse interrogation sequence.

14. The method of claim 13 wherein the interrogation involves a dual pulse interrogation having time spacing of 90 degrees-$\tau$-180 degrees.

15. The method of claim 6 wherein the NMR response is obtained from hydrogen in water in the tissue, the water being found in the healthy tissue and in cancerous tissue, and NMR responses are obtained from adjacent segmented portions of the female breast, the method including the step of subtracting output signals of adjacent breast portions to obtain a difference signal.

* * * * *